United States Patent [19]

Schroeder

[11] 4,043,997

[45] Aug. 23, 1977

[54] METHOD FOR ISOLATING ALBUMIN USING INSOLUBLE SUPPORTS COUPLED TO A DYE

[75] Inventor: Duane D. Schroeder, Orinda, Calif.

[73] Assignee: Cutter Laboratories, Inc., Berkeley, Calif.

[21] Appl. No.: 691,172

[22] Filed: May 28, 1976

[51] Int. Cl.² ............................................. C07G 7/00
[52] U.S. Cl. ................................................. 260/122
[58] Field of Search ................................. 260/122, 121

[56] References Cited

U.S. PATENT DOCUMENTS 4,016,149   4/1977   Travis et al. .................... 260/122

OTHER PUBLICATIONS

Clin. Chim. Acta, 49, pp. 49–52, 1973, Travis et al.
Chem. Abstracts, vol. 83, 1975, 24718e, Travis et al.

*Primary Examiner*—Howard E. Schain
*Attorney, Agent, or Firm*—Robert E. Allen; Bertram Bradley

[57] ABSTRACT

A method for the isolation of albumin which allows the selective adsorption and substantially quantitative elution of albumin from mixtures containing the same. The method comprises contacting a solution which contains albumin with a member of a series of dye-insoluble support compounds in which the insoluble support is a polyhydroxy polymer coupled to a dye by means of a reactive pyrimidine. The albumin which is selectively adsorbed can be readily eluted resulting in essentially a quantitative recovery of pure albumin.

16 Claims, No Drawings

METHOD FOR ISOLATING ALBUMIN USING INSOLUBLE SUPPORTS COUPLED TO A DYE

BACKGROUND OF THE INVENTION

This invention relates to a method for the selective adsorption of albumin from mixtures containing same and for substantially quantitative elution of the albumin by the use of a new series of dye-insoluble support compounds.

Albumin is a major protein in blood plasma or serum and is a commercially important product used in the medical field. The well known Cohn process or modifications thereof is generally employed in the fractionation of plasma into a number of medically useful and important protein fractions in addition to the production of albumin. Albumin, being one of the most soluble proteins, is among the last to be isolated in this long and tedious fractionation procedure for obtaining a variety of different plasma proteins. As a result, other methods have been sought for separating albumin from plasma, without sacrificing or being detrimental to the remaining proteins, which would be faster and more economical. In addition, it is frequently desired to isolate specific plasma components such as enzymes which are free of the major contaminant, albumin.

Recently a method has been described which indicated albumin in plasma could be selectively adsorbed onto and eluted from insoluble compounds which are made from a specific class of dyes coupled to agarose (German Offenlegungsschrift 2443119 filed Sept. 9, 1974; J. Travis and R. Pannell, Clin. Chim. Acta 49, pp. 49–52, 1973). This class of dyes is characterized by each dye having a triazine nucleus which is substituted with sulfonated aniline or naphthylamine groups. One of the dye-agarose compounds described is Sepharose 4B which is first activated with cyanogen bromide and then coupled to Blue Dextran. Blue Dextran is Cibacron Blue F3G-A in which the chlorine atom on the triazine moiety has been replaced with O-Dextran. The Sepharose 4B-Blue Dextran compound is reported to adsorb 96% of the albumin from plasma with substantially no adsorption of the other protein components. The albumin was about 80% eluted using a phosphate-ethanol eluting solvent at pH 2.4. A number of other dye-agarose compounds are disclosed including Cibacron Blue F3G-A coupled to cross-linked Sepharose 4B. Although a number of solutes are disclosed for eluting albumin, including a mixture of octanoic acid, Tris hydrochloride and sodium chloride, calcium, magnesium or potassium chloride with Tris hydrochloride, and high molar concentrations of aqueous area, no details are given on the efficiency of elution.

Although this method of Travis et al appears useful for selectively removing albumin from mixtures of proteins, the recovery of albumin is not sufficiently high to warrant the use of this process on a commercial scale. In addition, there is no indication as to the effectiveness in selective adsorption of albumin from protein solutions other than from plasma if the solutions contain higher or lower percentages of albumin as in certain Cohn fractions, e.g. crude gamma globulin, Cohn Fractions IV-1, IV, IV-4, the protein in Supernatant II + III, and Plasmanate® (plasma protein fraction isolated from Cohn Supernatant IV-1).

SUMMARY OF THE INVENTION

It has been found that a specific class of dyes when coupled chemically to certain insoluble polymeric supports provide dye-support compounds which not only selectively adsorb albumin from mixtures of protein solutions containing albumin but also allow albumin to be eluted substantially quantitatively. This improved characteristic with respect to the elution of albumin from the adsorbing compounds is unexpected since the structure of the dyes which form the dye-support compounds used in the process of the present invention and the dyes in the dye-supports used by Travis et al are not remarkably different. One structural difference is that a dye is bound to a support by a pyrimidine nucleus in the compounds used in the present invention whereas the prior art compounds have a triazine nucleus connecting a dye to a support.

DETAILED DESCRIPTION OF THE INVENTION

In the process of the present invention, albumin is quantitatively and selectively adsorbed from protein solutions containing the same by contacting said solutions with an insoluble compound of the general formula

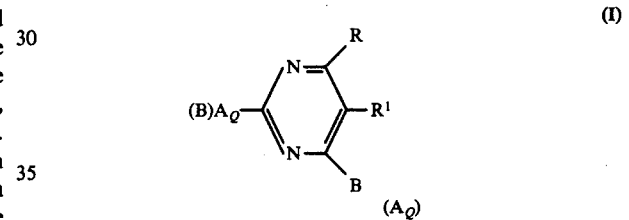

and separating the albumin-adsorbed compound from the aqueous phase. The process of this invention also includes the additional step of treating the albumin-adsorbed compound with an eluent which substantially removes all the albumin from the dye-support compound.

In general formula I, A and B are different and are interchangeable relative to their positions on the pyrimidine ring; A is a support comprising an insoluble polymer having hydroxyl groups, some of which have been replaced by ether linkages connected to the 2 or 4-position of the pyrimidine nucleus; B is a dye moiety of the general formula

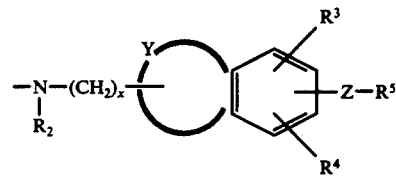

substituted at either the 4 or 2-position of the pyrimidine nucleus; R is halogen, e.g., fluorine or chlorine, or lower alkyl ($C_1$ to $C_4$); $R^1$ is hydrogen, halogen, e.g., fluorine or chlorine, $SCH_3$ or lower alkyl ($C_1$ to $C_4$); $R^2$ is hydrogen or lower alkyl ($C_1$ to $C_4$); $R^3$ and $R^4$ may be the same or different and selected from the group consisting of hydrogen, hydroxy, lower alkyl ($C_1$ to $C_4$), lower alkoxy ($C_1$ to $C_4$), and $—SO_3M$; X may be 0 or 1;

Y is [—H]$_2$ or —CH=CH—Ch=CH—; Z is —NH or —N=N—; R$^5$ is substituted aryl, e.g.,

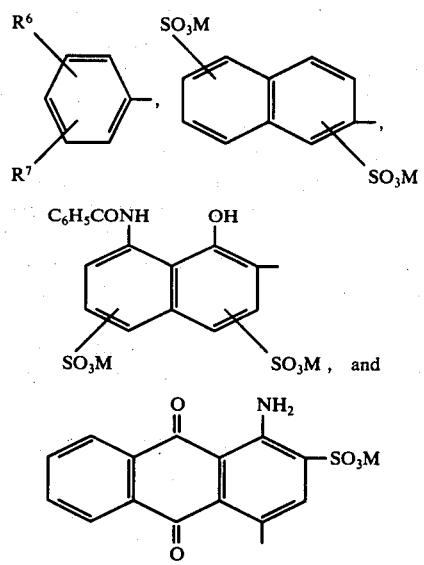

where R$^6$ and R$^7$ may be the same or different and are selected from the group consisting of hydrogen, lower alkyl, lower alkoxy and SO$_3$M; M is hydrogen or alkali metal; and Q is a weight ratio of the insoluble polymer A to the dye moiety B ranging from 1:1 to 50:1.

In the process of the present invention, the two embodiments of insoluble dye-support compounds used for selectively adsorbing albumin from protein solutions containing the same are either represented by general formula II

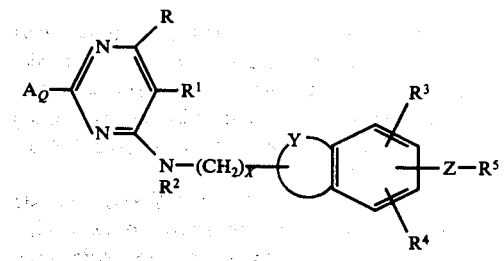

(II)

or by general formula III

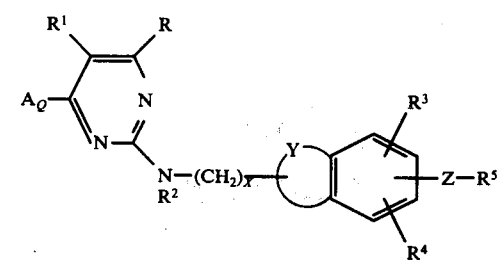

(III)

wherein A, R, R$^1$- R$^5$, X, Y, Z, and Q all have the same meaning as in formula I above.

The polymer A used as the support to which the dye is coupled can be any insoluble polymer which has a number of hydroxyl groups. Including but not limited to such polymers are agarose, crosslinked agarose and modified dextrans such as those supplied by Pharmacia Fine Chemicals under the trade names of Sepharose gels, grades 2B, 4B, and 6B, crosslinked Sepharose gels, grades CL-2B, CL-4B, and CL-6B, and Sephadex gels, grades G-75, G-100, G-150 and G-200, respectively. Any hydroxyl-bearing insoluble polymer should have a sufficient pore size to permit albumin to enter the pores to become adsorbed onto the dye which is coupled to the support structure within the pores. The various grades of Sepharose and Sephadex gels listed fall well within this requirement. The Sephadex gels are generally preferred.

The dye-support compounds of general formula II are prepared by the reaction scheme

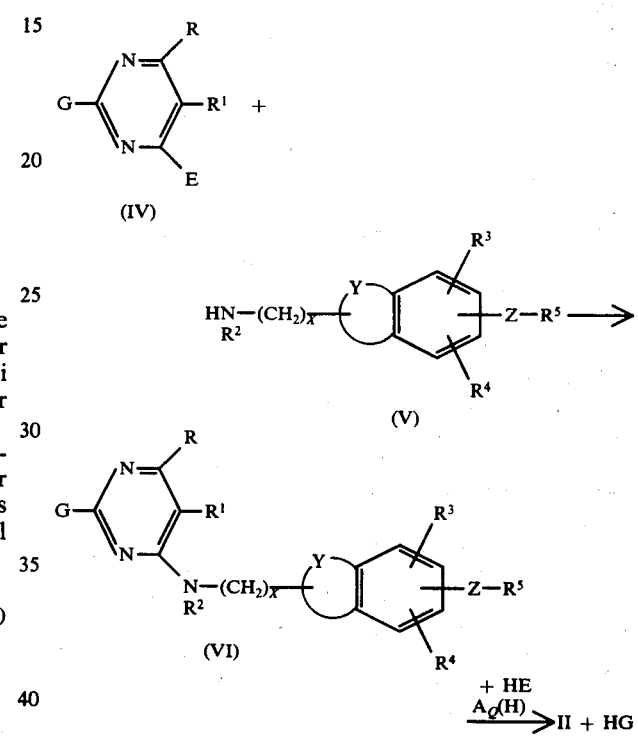

wherein E is a halogen atom, preferably fluorine, and G is a halogen atom, preferably fluorine, or another reactive group such as —SO$_2$CH$_3$. A number of (H) atoms of hydroxyl groups on the support A are replaced with the reactive dye VI. A preferred member of pyrimidine coupling agents IV is 2,4,6-trifluoro-5-chloropyrimidine.

The dye-support compounds of general formula III are prepared by the scheme prepared by the scheme

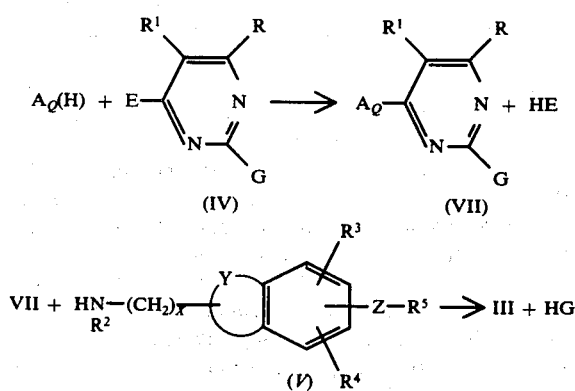

The reaction of the coupling agent IV with either dye V or support A is conducted generally at ambient temperatures or below in an alkaline medium. For example, IV can be added to a basic aqueous solution of dye V at about 20°-30° C and with the pH of the reaction mixture being maintained at about neutrality with the addition of sodium carbonate solution.

The coupling of reactive dye VI with support A is conducted by adding an aqueous solution of the reactive dye to a buffered aqueous suspension of the insoluble support at somewhat elevated temperatures and continuing the coupling reaction with stirring for a few minutes to an hour or so. The coupled product II is then thoroughly washed with hot water followed by a wash with Tris buffer containing sodium azide as bacteriostatic agent. The moist dye-support compound is used at once or it can be stored at about 5° C for indefinite periods.

The proportions of reactants, concentrations, time and temperatures do not appear to be critical. For example, the ratio of the weight of the reactive dye to the weight of the insoluble support can vary, i.e., between about 0.1 to 5 g. of dye per 5 g. of the insoluble support. Too little of the dye would result in a wasteful utilization of the support whereas too high an amount of dye would be wasteful of the dye. Between 0.5 and 1.5 g. of the reactive dye, per 5 g. of support is a preferred ratio. Since Sepharose gels are supplied as suspensions, measurement by volume rather than weight is more convenient. Thus 100 ml. of settled Sepharose 4B gel corresponds to about 4 g. of dry support.

The solution of reactive dye is generally made up to about a 5% solution although more dilute or concentrated solutions can be used. The suspension of insoluble support can vary over a wide range although about a 2% suspension appears most convenient. The coupling reaction occurs at a pH of about 7 to 10 which is provided by the addition of a suitable buffer such as sodium carbonate or other alkali. The temperature of the reaction may be between about 45° and 85° C, preferably no more than 65° C when Sepharose gels are used since they tend to melt at about 70° C. If higher temperatures are employed, e.g., about 85° C, then a crosslinked Sepharose gel should be used. With Sephadex gels, the upper limits can be used (85° C), although reaction is rapid at lower temperatures with 50°-60° C being preferred.

In the practice of removing albumin from aqueous protein mixtures containing the same, the albumin is selectively adsorbed onto a dye-support compound using either a batch or column operation. Either operation is convenient on a commercial scale. The dye-support compound is first equilibrated with a solution of suitable ionic strength, such as sodium chloride, Tris-HCl/sodium chloride buffer, sodium carbonate or phosphate buffer, usually in a pH range between 6.5 and 8.5, preferably at about 8.0.

The starting material from which albumin can be removed may be a number of different protein solutions containing varying percentages of albumin including: human plasma; Supernatant II + III (from the Cohn process; E. J. Cohn et al, J. Am. Chem. Soc., 68, 459 (1946); mixtures containing predominately globulins and albumin, including Plasmanate® protein fraction (U.S. Pat. No. 2,958,628); Cohn Fractions IV-1, IV, and IV-4 (from the Cohn process); and slightly impure human albumin. The utility of the process of the present invention is not limited to the above-named mixture as starting materials, e.g., albumin from mixtures other than those derived from humans can be used. The process is also useful for the purification of enzymes and other biological products in which crude enzymes or other impure products are contaminated with albumin.

After the equilibration of the dye-support compound, the albumin-containing protein solution is allowed to come in contact with the dye-support compound. Generally, the protein solution is allowed to come in contact with about 10 ml. of settled dye-support compound in an amount of the solution which contains about 100 mg. of albumin. Smaller or larger quantities of albumin per 10 ml. dye-support are also possible, e.g., about 10 to about 500 mg./10 ml. is usually a preferred range. The adsorption of the albumin on the dye-support compound can be conducted either by a batch or a column procedure and required only a very brief period of contact time of about a minute to several minutes to effect substantially quantitative adsorption of the albumin. In a column procedure, flow rates may be quite rapid.

Following adsorption, in the case of batch operations, the supernatant liquid is removed by decantation or filtration, etc. and the dye-support compound is washed free of any unadsorbed proteins, for example with 0.05 M Tris-HCl buffer. With column operations, the buffer is allowed to flow through the column until the absence of protein is observed, conveniently by analyzing the washes by U.V. absorbance at 280 nm.

The process of the present invention further includes eluting substantially quantitatively the albumin which is adsorbed on the dye-support compound with suitable eluting agents which do not alter the albumin and which are physiologically acceptable. The improvement of the eluting step in the present invention over the prior art, i.e., the substantially quantitative removal of the albumin from the dye-support compound, is believed to relate to the albumin being less firmly bound to the dye portion of the compound used in the present process. The strength of binding of the albumin to the dye is however great enough that all the albumin from albumin-containing protein mixtures is absorbed onto the dye-support compound. The dye-support compounds used in the present invention are capable of repeated use following elution of the albumin, i.e., they maintain their adsorptive properties for further removal of albumin from protein mixtures containing albumin.

The elution of the adsorbed albumin is substantially quantitative wherein albumin is obtained essentially pure. The elution may be accomplished with a variety of different types of eluting agents including basic buffered solutions of fatty acids of which caprylic acid is a preferred member since it also is a good stabilizer for albumin. Among other suitable eluting agents are solutions of electrolytes, preferably those which are also physiologically acceptable such as sodium chloride, sodium phosphate, etc., generally having an ionic strength about 0.2 M to about 1.0 M. Still other effective eluting agents are amino acids such as, tryptophane, N-acetyltryptophane, glycine with sodium chloride, and thiocyanate, calcium, potassium, and magnesium salts and ammonium bicarbonate or sodium carbonate. These latter salts, though effective, would not be physiologically acceptable in a final product and would have to be removed as by dialysis, ultrafiltration or other means before the albumin would be suitable for parenteral use.

The pH of the eluting agent should generally be between about 6.0 and 8.5, preferably about pH 8.0, although a lower pH is also effective. Maintenance of the preferred pH can be brought about by the inclusion of a buffer, as for example sodium bicarbonate, sodium phosphate or Tris-HCl. The amount of eluting agent necessary to substantially remove all the adsorbed albumin may vary depending upon the specific elutant used. Completion of elution can be readily determined by following U.V. absorbancy at 280 nm of the eluate. The eluate, containing the albumin which is essentially pure or free of other proteinaceous material, can be concentrated by methods well known in the art such as by precipitation, diafiltration,, ultrafiltration, etc., which procedures also remove some or all the material used as eluting agent from the albumin. Concentrated solutions of the albumin containing appropriate stabilizing agents can be heat treated to destroy any hepatitis virus which may be present, sterile filtered and lyophilized to provide pure dry albumin. Alternatively, the heat treated eluate can be concentrated to a concentration suitable for parenteral use, e.g. 5%, to be sterile filtered into vials.

The dye-support compounds used in the process of this invention can be used repeatedly merely by re-equilibrating with a suitable solution, e.g., Tris-HCl between 0.05 and 0.1 M, sodium chloride, etc.

Some of the reactive dyes VI used for coupling to insoluble support A include the following:

Table 1

| Reactive Dye | Number |
|---|---|
| (anthraquinone dye structure) | RD-1 |
| (anthraquinone dye structure) | RD-2 |
| (anthraquinone dye structure) | RD-3 |
| (anthraquinone dye structure) | RD-4 |
| (naphthalene azo dye structure) | RD-5 |

Table 1-continued

| Reactive Dye | Number |
|---|---|
| [Structure: naphthalene with HO₃S, OH, azo group to CH₃O-phenyl-SO₃H, and NH-chlorofluoropyrimidine substituents] | RD-6 |
| [Structure: naphthalene with C₆H₅CNH (O), OH, SO₃H, SO₃H groups, azo linkage to phenyl-SO₃H with NH-chlorofluoropyrimidine] | RD-7 |

The invention can be more fully understood by some preferred embodiments as detailed in the examples hereinbelow.

PREPARATION OF REACTIVE DYES (RD)

A. Preparation of RD-1

A solution of 38.2 g. of 1-amino-4-bromo-2-anthraquinonesulfonic acid (available from Pfaltz & Bauer, Inc., Flushing, N.Y.) and 1.5 g. of cupric chloride in 750 ml. water was added to a solution of 38 g. of m-phenylenediamine, 20 g. sodium sulfite and 25 g. sodium carbonate in 250 ml. water. The mixture was stirred under nitrogen at room temperature for 6 to 8 hours, clarified with charcoal, and the condensation product was precipitated with the addition of 220 g. sodium chloride.

To a solution of 40.9 g. of the condensation product, 1-amino-4(3'-aminoanilino)anthraquinone-2-sulfonic acid, in 300 ml. water was added 26.5 g. of 2-methylsulfonyl-4,5-dichloro-6-methylpyrimidine (German Pat. No. 2,242,507). The mixture was warmed to 50° C and the hydrochloric acid as it formed was neutralized with sodium carbonate solution. The coupled product was dried, pulverized, and 220 ml. of 15% fuming sulfuric acid was added, keeping the mixture below 30° C with cooling. The mixture was added to 500 g. ice, the precipitate was filtered, dissolved in 200 ml. water, neutralized with sodium hydroxide, heated to 75° C and treated with 10% saline. With cooling, the reactive dye RD-1 was obtained having the structure as shown previously in Table I.

B. Preparation of RD-2

The procedure was the same as described in Preparation A (above) for the synthesis of 1-amino-4(3'-aminoanilino) anthraquinone- -2-sulfonic acid. To a solution of 8.2 g. of this intermediate in a mixture of 160 ml. water, 80 ml. dioxan and 1.05 g. sodium carbonate was added dropwise 3.8 g. 2,4,6-trifluoro-5-chloropyrimidine at 0° C. The pH of the mixture was maintained between 6.0 and 6.5 by the addition of 2N sodium carbonate solution. The reaction product was salted out by the addition of 5 g. sodium chloride at 20° C, washed with 2% sodium chloride solution and dried at 30° C. Ten grams of the dried product was added slowly to 70 g. of 13% oleum at 0° C, allowing the temperature to rise to about 20° C near the end of the reaction. The mixture was poured into 220 g. of ice-water containing 30 g. potassium chloride. The precipitated product was filtered and washed with saturated potassium chloride solution until neutral to give the reactive dye RD-2 having the structure shown in Table I.

The 2,4,6-trifluoro-5-chloropyrimidine is obtained by the procedure described in British Pat. No. 1,157,948.

C. Preparation of RD-3

Following the procedure analogous to that in Preparation A, 1-amino-4-bromo-2-anthraquinonesulfonic acid was condensed with 2,6-diaminotoluene-4-sulfonic acid, the synthesis of the latter compound being described by Buckel, Chem, Zentr. 28, p. 1410 (1904). This condensed product was then coupled with 2,4,6-trifluoro-5-chloropyrimidine analogous to the procedure described in Preparation B to give the reactive dye RD-3 having the structure shown in Table I.

D. Preparation of RD-4

By a procedure analogous to that described in Preparation A, 1-amino-4-bromo-2-anthraquinonesulfonic acid was condensed with 3-methylaminomethyl-4-methoxyaniline, the synthesis of the latter compound being disclosed in German Pat. No. 2,107,914. The condensed product was sulfonated by the procedure described in Preparation A. Approximately a 5% aqueous solution of the sulfonated product was reacted with a molar equivalent of 2,4,6-trifluoro-5-chloropyrimidine at 20° to 25° C, keeping the pH between 6.0 to 6.5 by the addition of sodium carbonate. Sodium chloride was added to the reaction mixture which was adjusted to pH 5.0 until precipitation appeared complete. The crystalline product was filtered, washed with 15% sodium chloride solution, and dried to give the reactive dye RD-4 having the structure shown in Table I.

E. Preparation of RD-5

To 27 g. of the sodium salt of 2-amino-5-hydroxynaphthalene-7-sulfonic acid (J-acid, available from Eastman Organic Chemicals, Rochester, N.Y.) in 150 ml. water was added 20 g. of 2,4,6-trifluoro-5-chloropyrimidine with stirring at 30° C while neutralizing the hydrogen fluoride as it is formed by the addition of 34 ml. of 16% sodium carbonate solution. When the reaction is complete, 30 g. of sodium bicarbonate is added. A suspension of the diazonium salt prepared from 34 g. of the disodium salt of 2-aminonaphthalene-1,7-disulfonic acid (synthesis of the amine described by Bucherer et al, J. Pract. Chem. (2) 103, 144 (1868) in 200 ml. water was added dropwise at 20° C in 15 minutes. Following the addition of 80 g. of sodium chloride, the mixture was stirred 1 hour, the precipitated dye was filtered, washed with dilute sodium chloride solution and dried at 35° C to give reactive dye RD-5 having the structure shown in Table I.

F. Preparation of RD-6

By the same procedure described in Preparation E, J-acid was condensed with 2,4,6-trifluoro-5-chloropyrimidine. This intermediate was then coupled to diazotized 2-amino-5-methoxybenzenesulfonic acid (synthesis of this amine described in Chem. Zentr., 1903 II, p. 1301) by a procedure similar to that described in Preparation E. Reactive dye RD-6 was obtained having the structure as shown in Table I.

G. Preparation of RD-7

To a solution of 21 g. of the sodium salt of 2,4-diaminobenzenesulfonic acid in 100 ml. water (synthesis of this amine described by Post et al, Ann. der Chem. 205, 107 (1880) was added with rapid stirring 20 g. of 2,4,6-trifluoro-5-chloropyrimidine at 20°-30° C while neutralizing the hydrogen fluoride as it was formed. The resulting product was diazotized using 7 g. sodium nitrite and 28 g. hydrochloric acid, then added to a solution of 47 g. of the sodium salt of 1-hydroxy-8-benzamidonaphthalene-3,5-disulfonic acid (synthesis described by Brieger et al, J. Pract. Chem. (2) 89, 165 (1863) and 12 g. sodium carbonate in 200 ml. water. The coupled product was salted out, filtered, washed with saline and dried to give the reactive dye RD-7 having the structure shown in Table I.

DYE-SUPPORT COMPOUND OF GENERAL FORMULA II

EXAMPLE 1

Preparation of Crosslinked Sepharose 4B

By the procedure described by J. Porath et al, J. Chromatogr. 60, 167 (1971), 1 liter Sepharose 4B (volume of moist settled gel) is suspended in 1 liter of 1 N sodium hydroxide containing 5 g. sodium borohydride. With gentle stirring, 20 ml. of epichlorohydrin is added and the mixture is heated to 60° C for an hour. The crosslinked Sepharose 4B thus obtained is washed with hot water until neutral.

EXAMPLE 2

Coupling of Reactive Dye to Crosslinked Sepharose 4B

By the procedure described by H.J. Boehme et al, J. Chromatogr. 69, 209 (1972), 20 ml. of the moist crosslinked Sepharose 4B gel slurried in 20 ml. water is warmed to 65°- 70° C. With stirring, a solution of 0.2 g. of a reactive dye in 10 ml. water is added, followed by 20 ml. of a solution containing 75 g. sodium chloride and 15 g. sodium carbonate per liter. The reaction is continued for about an hour at 65°- 70° C. The dye-Sepharose 4B compound is filtered, washed with hot water until the washes are colorless, then washed with Tris-HCl buffer (0.05 M Tris-HCl, 0.5 M sodium chloride, pH 8.0) containing 0.02% sodium azide. After filtering, the moist compound can be stored indefinitely at 5° C.

The following Reactive Dye-Crosslinked Sepharose 4B compounds are obtained:

| Example 2 | Reactive Dye coupled to Crosslinked Sepharose 4B |
|---|---|
| A | RD-1 |
| B | RD-2 |
| C | RD-3 |
| D | RD-4 |
| E | RD-5 |
| F | RD-6 |
| G | RD-7 |

EXAMPLE 3

Coupling of Reactive Dye to Sephadex G-100

The procedure used is similar to the procedure described for coupling a Reactive dye to crosslinked Sepharose 4B (Example 2) except milder conditions are employed. Sephadex G-100 (10 g. dry powder) is suspended in 500 ml. water at 50°- 60° C until swelling appears complete, then a solution of 2.5 g. of a Reactive dye in 50 ml. water is added to the stirred gel. To the mixture is then added 20 g. sodium chloride and 5.0 g. sodium carbonate and stirring at 50°-60° C is continued for about one to two hours. The compound is filtered, washed free of excess dye, followed by a wash with Tris-HCl buffer and stored at 5° C.

The following Reactive dye - Sephadex G-100 compounds are obtained:

| Example 3 | Reactive Dye coupled to Sephadex G-100 |
|---|---|
| A | RD-1 |
| B | RD-2 |
| C | RD-3 |
| D | RD-4 |
| E | RD-5 |
| F | RD-6 |
| G | RD-7 |

PRIOR ART DYE-SUPPORT COMPOUNDS

EXAMPLE 4

Cibacron Blue F3G-A Coupled to Crosslinked Sepharose 4B

The procedure described in Example 1 of German Offenlegungsschrift 2443119 is followed using Cibacron Blue F3G-A (Procion Blue HBS) in place of Cibacron Brilliant Blue FBR-P. One hundred milliliters of settled crosslinked Sepharose 4B (from Example 1, supra) is suspended in 250 ml. of water. A solution of 1.0 g. Cibacron Blue F3G-A (obtained from Ciba-Geigy, Basel, Switzerland) in 25 ml. water is added and the mixture is agitated gently at 80° C for 45 minutes. The pH is maintained at about 8.0 by the addition of sodium carbonate. After cooling to room temperature, the supernatant liquid is decanted and the solid phase is washed first with 3 L. water, then with 2 L. of 5M guanidine hydrochloride solution, and finally with a solution containing 0.05 M Tris-hydrochloride and 0.5 M sodium chloride. The Cibacron Blue F3G-A - crosslinked Sepharose 4B compound thus obtained is used as the control in a comparison with the dye-support compounds of this invention in the process of this invention as described hereinafter.

EXAMPLE 5

Cibacron Blue F3G-A Coupled to Sephadex G-100

The procedure is the same as that of Example 3 except 2.5 g. of the dye Cibacron Blue F3G-A (obtained from Ciba-Geigy, Basel, Switzerland) is used in place of a reactive dye. The coupled product is similar to the dye-support compound of Example 4, the support being Sephadex instead of crosslinked Sepharose.

ADSORPTION AND ELUTION OF ALBUMIN

EXAMPLE 6

Removal of Albumin from Plasma

A solution of 0.1 ml. human plasma in 3.0 ml. Tris-HCl buffer (0.05 M Tris-HCl + 0.15 M sodium chloride, pH 8.0) is added to each of 1.0 ml. of a moist settled Reactive dye - cross-linked Sepharose 4B compound in test tubes. The contents are occassionally swirled and after 30 minutes, the solid compounds are collected by Centrifugation, the supernatant solution is removed and the solids are washed twice with 3.0 ml. portions of Tris-HCl buffer. The supernatant and washes and combined in each case and the absorbancy read in a U.V. spectrophotometer to determine the amount of protein unadsorbed by the compound. Each compound is then swirled occassionally for 10 minutes in 3 ml. of a solution containing 0.2 M sodium thiocyanate and 0.05 M Tris-HCl buffer. The thiocyanate-buffer supernatants are also read by U.V. to determine the amount of albumin eluted. Both the composite washes and the eluates are additionally tested by cellulose acetate electrophoresis to determine the degree of adsorption onto and the degree of elution of albumin from a particular compound. One ml. quantities of crosslinked Sepharose 4B and Cibacron Blue F3G-A crosslinked Sepharose 4B are treated as above to serve as controls.

Electrophoretic patterns all indicated the eluted albumin to be substantially pure. In general, the dye-Sepharose compounds of the present invention adsorb albumin from plasma as effectively as the complex of Example 4 and generally allow a greater degree of elution than does the compound of Example 4. (See Table II).

EXAMPLE 7

This example is essentially a repeat of Example 6 except with minor modifications. A much smaller amount of eluting agent is used to obtain a more concentrated solution of albumin suitable for purity analysis by cellulose acetate electrophoresis. The dye-support compounds (1.0 ml.) are treated with 0.2 ml. of human plasma in 3.0 ml. Tris-HCl buffer for about 2 minutes and then washed four times with the buffer. The albumin is eluted with only 0.5 ml. of the thiocyanate Tris-HCl eluting solution. The results are shown in Table III.

TABLE II

| Dye-Support Compound | Absorbancy at 280 nm | Unbound protein, percent | Absorbancy of eluate (1) | Relative Elution Efficiency | Electrophoretic Pattern, degree of: Absorption | Elution |
| --- | --- | --- | --- | --- | --- | --- |
| Example 4 (Control) | 0.685 | 56.8 | 0.137 | 1.0 (2) | + + | + + |
| Example 1 (Control) | 1.205 | 100.0 | 0.000 | — | — | — |
| Example 2A | 0.910 | 75.5 | 0.161 | 1.18 | + | + + |
| Example 2B | 0.755 | 62.7 | 0.157 | 1.15 | + + | + + |
| Example 2C | 0.658 | 54.6 | 0.309 | 2.25 | + + | + + + |
| Example 2D | 0.788 | 65.4 | 0.267 | 1.95 | + + | + + + |
| Example 2E | 0.932 | 77.3 | 0.112 | 0.82 | + | + |
| Example 2F | 1.000 | 83.0 | 0.114 | 0.83 | + | + |

(1) Absorbancy of eluate minus absorbancy of thiocyanate alone (0.026)
(2) Assigning a value of 1.0 to the control (Example 4)

TABLE III

| Dye-Support Compound | Absorbancy of unbound protein at 280 nm | Absorbancy of eluate | Relative Elution Efficiency | Electrophoretic Pattern, degree of Elution |
| --- | --- | --- | --- | --- |
| Example 4 | 2.147 | 1.110 | 1.0 | + |
| Example 2A | 2.789 | 0.148 | 1.35 | + + + |
| Example 2B | 2.262 | 0.224 | 2.04 | + + |
| Example 2C | 2.207 | 0.700 | 6.36 | + + + + |
| Example 2D | 2.397 | 0.540 | 4.91 | + + + + |
| Example 2E | 2.985 | 0.400 | 3.64 | + + + + |
| Example 2F | 2.983 | 0.376 | 3.42 | + + + |
| Example 2G | 2.698 | 0.272 | 2.47 | + + + |

All Reactive dye - crosslinked Sepharose 4B compounds demonstrate weaker binding of albumin than does the dye-support compound of Example 4. This desirable chaaracteristic allows albumin to be eluted more effectively.

EXAMPLE 8

This example illustrates the application of the process of the invention on a protein mixture which contains a higher percentage of albumin than does plasma. Two compounds of different binding strength (Examples 2D and 2E) are compared with the control (Example 4). A column procedure is used.

Pasteur pipettes having a volume of 1.8 ml. are packed with the selected dye-crosslinked Sepharose 4B compounds and equilibrated with Tris-HCl buffer. To the separate pipettes is applied 0.5 ml. of either a solution of human plasma diluted 50% with Tris-HCl buffer or a 1% buffered solution of human plasma protein fraction (Plasmanate protein fraction from Cutter Laboratories, Inc., Berkeley, Calif., which contains about 83% albumin and about 17% alpha and beta globulins). This is followed with 1.0 ml. of Tris-HCl buffer and the next 0.5 ml. of eluate is collected as void volume for analysis of unbound protein. An additional 2.5 ml. of buffer is allowed to flow through which is then followed by 1.0 ml. of the eluting solution (0.2 M sodium thiocyanate, 0.05 M Tris-HCl) and then additional eluting solution, collection the next 1.0 ml. which contains the albumin.

TABLE IV

| Dye-Support Compound | Protein Used | Albumin Content by Electrophoresis Void Volume | Eluate | Absorbancy of wash solution, unbound protein |
|---|---|---|---|---|
| Example 4 | Plasma | — | ++ | 0.940 |
| | Plasmanate | — | ± | 0.074 |
| Example 2D | Plasma | ± | ++++ | 1.000 |
| | Plasmanate | — | +++ | 0.080 |
| Example 2E | Plasma | ++++ | ++++ | 1.450 |
| | Plasmanate | — | +++ | 0.105 |

The results indicate that certain dye-support compounds of the invention have greater utility than the compound of Example 4 when used on protein mixtures containing a higher proportion of albumin. For example, the dye-support compound of Example 2D adsorbs albumin essentially quantitatively as does that of Example 4, but the recovery of albumin is much superior.

EXAMPLE 9

This example shows the effectiveness of Reactive dyes which are coupled to Sephadex G-100 as support. The dye-support compound is packed in 1.6 × 20 cm. columns, equilibrated with Tris-HCl buffer and various protein mixtures applied to the columns at a rate of about 25 ml./hour. Columns 1 through 4 received approximately 2.0 ml. of human plasma; columns 5, 6 and 23 received a solution of 100 mg. Plasmanate powder dissolved in 3.0 ml. water adjusted to pH 8.0 with sodium hydroxide; columns 7 through 10 received 3.0 ml. of a solution containing 150 mg. of the protein mixture obtained by lyophilization of Cohn Supernatant II + III; columns 11 through 14 received a solution of 150 mg. Cohn Fraction IV in 3.0 ml. adjusted to pH 8.0; columns 15 through 17 received a solution of 150 mg. of Cohn Fraction IV-4 in 3.0 ml. adjusted to pH 8.0; and columns 18 through 22 received 3.0 ml. each of solutions of slightly impure human albumin (100 mg., pH 8.0). Following the application of the protein mixtures, Tris-HCl buffer is passed through the columns, constantly monitoring the eluate by U.V. When the absorbancy of the eluate indicates no further passage of unabsorbed protein, the usual buffered thiocyanate eluting solution is applied and the eluate monitored.

The results in Table V show the generally high degree of utility of a Reactive dye - Sephadex gel compound in the process of isolating pure albumin in high yield from mixtures of proteins regardless of the composition of the mixture or the proportion of albumin in the mixture. The data also show the compounds of this invention can be used to isolate albumin conveniently on starting materials (e.g., Supernatant II + III) available much earlier in the Cohn fractionation process and thereby avoid the much longer and expensive Cohn process leading to the preparation of albumin. Additionally, the data show that albumin can be recovered from fractions which normally are discarded following albumin isolation in the Cohn process, e.g., Fractions IV and IV-1. The known dye-support compound used in column 23 is included to compare it with compound 3A and 3D used in columns 5 and 6. The superiority of compounds 3A and 3D in the obtaining of pure albumin from the protein mixture Plasmanate is quite apparent.

Analysis by cellulose acetate electrophoresis of the eluates confirms the selectivity of adsorption on and the efficient elution of the albumin from these compounds. For example, in the experiments on columns 1 and 3, there is no detectable albumin in the unbound protein eluates and the thiocyanate eluates show only albumin in high yield. With columns 5 and 6 experiments, there was only a trace of albumin in the unbound eluates from column 5, none in column 6, and the thiocyanate eluates had only albumin in high yields.

TABLE V

| Column | Dye-Support Compound of Example: | Protein | Pattern* of U.V. Absorbancy at 280 nm | |
|---|---|---|---|---|
| | | | Unbound protein | Eluate |
| 1 | 3A | Plasma | L-sh,M-sh | M-sh |
| 2 | 3C | Plasma | L-b,M-sh,S-b | L-b-t |
| 3 | 3D | Plasma | L-sh,M-sh | L-sh |
| 4 | 3G | Plasma | L-sh,M-b-t | M-b-t |
| 5 | 3A | Plasmanate | ML-sh,M-sh | M-sh |
| 6 | 3D | Plasmanate | M-sh,S-b | L-sh |
| 7 | 3B | Supernatant II + III | L-sh,Msh | L-sh-t |
| 8 | 3C | Supernatant II + III | L-sh,M-sh | L-sh |
| 9 | 3D | Supernatant II + III | L-sh,S-b | L-b |
| 10 | 3G | Supernatant II + III | M-b,S-b | L-sh-t |
| 11 | 3B | Fraction IV | L-sh | M-sh |
| 12 | 3C | Fraction IV | L-b,M-b | ML-sh-t |
| 13 | 3D | Fraction IV | L-b-t | M-b |
| 14 | 3G | Fraction IV | L-b,S-b-t | L-b-t |
| 15 | 3B | Fraction IV-4 | L-sh,M-sh-t | ML-sh |
| 16 | 3C | Fraction IV-4 | L-sh,S-b-t | M-sh |
| 17 | 3D | Fraction IV-4 | L-b,S-b-t | M-b |
| 18 | 3A | Albumin, Human | ML-b,MS-t | M-sh |
| 19 | 3B | Albumin, Human | S-sh,VS-b | L-b-t |
| 20 | 3C | Albumin, Human | S-sh,VS-b | L-sh |
| 21 | 3D | Albumin, Human | S-t,VS-b | L-b |
| 22 | 3G | Albumin, Human | S-sh-t,VS-b | L-b-t |
| 23 | 4 | Plasmanate | M-b,S-b | S-b-t |

*The following letters designate the height (amount) and character of the continuous absorbancy of

TABLE V-continued

| Column | Dye-Support Compound of Example: | Protein | Pattern* of U.V. Absorbancy at 280 nm | |
|---|---|---|---|---|
| | | | Unbound protein | Eluate | the eluates: L=large, M=medium, S=small, ML=medium large, MS=medium small, sh=sharp, b=broad, t=tailing

EXAMPLE 10

High Ionic Strength Electrolytes as Eluting Agents

A solution of 100 mg. slightly impure human albumin in 3.0 ml. of Tris-HCl buffer is applied to a 1.6 × 20 cm. column packed with the dye-support compound of Example 3D. Tris-HCl buffer is then passed through the column followed by a solution containing 0.05 M Tris-HCl and 1.0 M sodium chloride. To determine whether the sodium chloride is completely eluting the adsorbed albumin, the column is further washed with 0.2 M and then 4.0 M sodium thiocyanate solutions. The unbound protein washes contain only very small amounts of protein (U.V. monitor) and the sodium chloride eluates show a very high, sharp peak. The 0.2 M thiocyanate eluate shows only a trace of albumin and the 4.0 M eluate contains no albumin. Sodium chloride is a very effective eluting agent for albumin absorbed on Reactive dye - Sephadex compounds.

The column is washed free of sodium thiocyanate and equilibrated with the usual Tris-HCl buffer. By the same procedure, albumin is absorbed onto the column and eluted with a solution containing 0.05 Tris-HCl and 0.2 M calcium chloride, followed by 0.2 M sodium thiocyanate. The albumin is completely eluted but there is some tailing. No additional albumin is eluted by the thiocyanate. This experiment shows calcium chloride is a good eluting agent and it also demonstrates the dye-support compounds of this invention can work effectively with repeated use following regeneration.

EXAMPLE 11

Carboxylic Acids and Amino Acids as Eluting Agents

Albumin is adsorbed onto the dye support compound as described in Example 10 and eluted with a solution containing 0.2 M DL-N-Acetyltryptophane and 0.05 M Tris-HCl buffer adjusted to pH 8.0 by sodium hydroxide. The albumin is essentially completely eluted but with some tailing. Subsequent washing with 0.2 M thiocyanate eluted less than 2% of the total albumin eluted.

Following regeneration of the column by Tris-HCl washes, albumin is again adsorbed as before and eluted with a solution containing 0.027 M sodium caprylate, followed by 0.02 M thiocyanate. The caprylate eluate shows essentially complete removal of the albumin with no tailing. The subsequent thiocyanate wash eluted less than 2% of the total amount of albumin.

EXAMPLE 12

This example shows the capacity of the dye-support compounds for binding albumin. Four sequential aliquots (2.0 ml.) each containing 100 mg. of slightly impure human albumin in water at pH 8.0 is applied to a column (0.9 × 14 cm.) containing 8 ml. of the moist settled dye-support compound of Example 3G. Trishydrochloride buffer is passed through following the application of each aliquot to remove any unbound protein and each wash is analyzed by U.V. A total of 5.9% of non-albumin protein is obtained as determined by U.V. and electrophoresis. The wash following the fourth aliquot contains a trace of albumin indicating the binding capacity had been reached. The binding capacity is thus about 400 mg. albumin per 8 ml. of dye-support compound or 50 mg. per ml.

The albumin is eluted with 0.2 M sodium thiocyanate in 0.05 M Tris buffer and by U.V. analysis 93.3 percent of the applied protein is recovered as albumin (judged pure by electrophoretic assay) indicating essentially quantitative recovery of the availble albumin in the sample.

EXAMPLE 13

This example illustrates the improved efficiency in the elution of albumin from the dye-support compounds of this invention as compared with a dye-support compound of the prior art. By the procedure described in Example 12, the slightly impure albumin is applied to columns of the dye-support compounds of Example 3G and Example 5 with the following results:

TABLE VI

| | Compound of Example 3G | Compound of Example 5 |
|---|---|---|
| Capacity for adsorbing albumin | about 50 mg./ml. | about 50 mg./ml. |
| Unbound protein | 5.9% | 8.2% |
| Albumin eluted | 93.3% | 74.8% |
| Albumin recovered | 99.2% | 83.0% |

What is claimed is:

1. A process for selectively removing albumin from aqueous fluids containing the same comprising the step of:

a. Contacting the albumin-containing fluid with a composition of the general formula

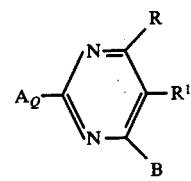

wherein A and B are different; wherein A is a support consisting of an insoluble polymer having hydroxyl groups and B is a dye having the formula

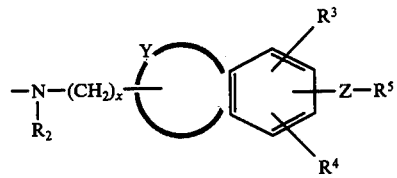

wherein R is halogen or lower alkyl; $R^1$ is hydrogen, $SCH_3$, halogen, or lower alkyl; $R^2$ is hydrogen or lower alkyl; $R^3$ and $R^4$ each are members of the group consisting of hydrogen, lower alkyl, lower alkoxy, hydroxy and $—SO_3M$; X is an integer from 0-1; Y is $—[H]_2$ or $—CH=CH—CH=CH—$; Z is —NH— or —N═M—; R⁵ is a substituted aryl selected from the group consisting of

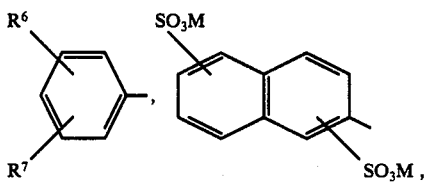

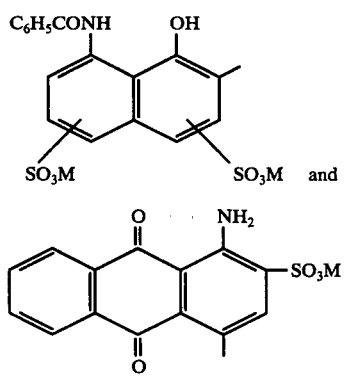

wherein R⁶ and R⁷ each are members of the group consisting of hydrogen, lower alkyl, lower alkoxy, and —SO₃M; wherein M is hydrogen or alkali metal; and wherein Q is a weight ratio of the insoluble polymer to the remainder of the compound of between 1:1 and 50:1;

b. adsorbing the albumin on the composition, and
c. separating the composition on which the albumin is adsorbed from the aqueous phase.

2. A process according to claim 1 wherein Q is a ratio between 3.75:1 and 10:1.

3. A process according to claim 1 wherein A is selected from the group consisting of agarose, crosslinked agarose and modified dextran.

4. A process according to claim 1 including the subsequent step of treating the composition on which albumin is adsorbed with an eluting solution containing a substance which substantially removes all the adsorbed albumin from the composition.

5. A process according to claim 4 wherein the substance is selected from the group consisting of a carboxylic acid containing up to 10 carbon atoms, an amino acid, physiologically acceptable inorganic electrolytes; and calcium, magnesium, potassium, thiocyanate and carbonate salts.

6. A process according to claim 5 wherein the carboxylic acid is caprylic acid.

7. A process according to claim 6 wherein the caprylic acid solution is at least about 0.02 M and the pH of the eluting solution is about 8.0.

8. A process acording to claim 5 wherein the inorganic electrolyte is sodium chloride.

9. A process according to claim 5 wherein the inorganic electrolyte solution has an ionic strength of about 0.2 to about 1.0 M.

10. A process according to claim 5 wherein the amino acid is N-acetyltryptophane.

11. A process according to claim 10 wherein the N-acetyltryptophane is at least about 0.02 M and the pH of the eluting solution is about 8.0.

12. A process according to claim 4 wherein the composition is a member of the general formula

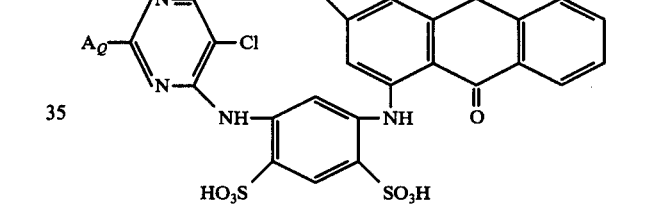

13. A process according to claim 12 wherein the composition is

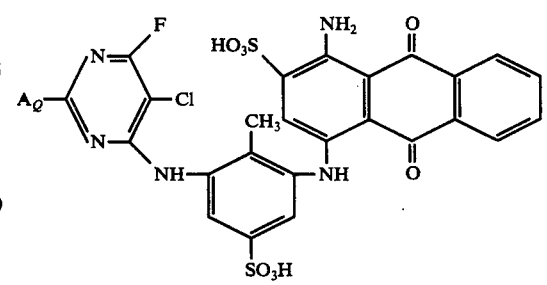

14. A process according to claim 12 wherein the composition is

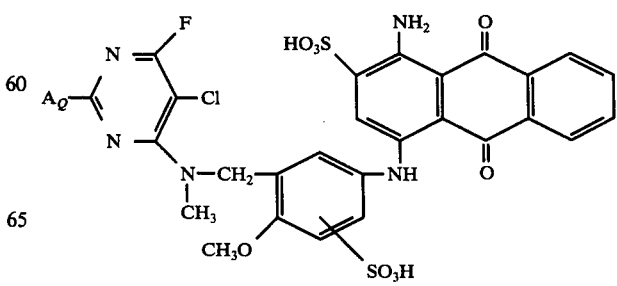

15. A process according to claim 12 wherein the composition is

16. A process according to claim 4 wherein the composition is
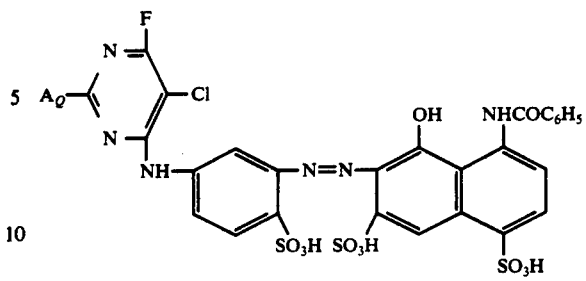
* * * * *

UNITED STATES PATENT AND TRADEMARK OFFICE
CERTIFICATE OF CORRECTION

PATENT NO. : 4,043,997
DATED : August 23, 1977
INVENTOR(S) : Duane D. Schroeder

It is certified that error appears in the above-identified patent and that said Letters Patent are hereby corrected as shown below:

Column 3, line 1, change "-CH=CH-Ch=CH-" to

-- -CH=CH-CH=CH- --.

Column 13, line 56, change "Centrifugation" to

-- centrifugation --.

Column 13, line 58, change "and" (second occurrence) to

-- are --.

Column 14, Table III, under the heading "Absorbancy of eluate", change "1.110" to -- 0.110 --.

Column 18, line 38, change "step" to -- steps --.

Column 19, line 1, change "-N=M-" to -- -N=N- --.

*Signed and Sealed this*

*Twenty-second* Day of *November 1977*

[SEAL]

Attest:

RUTH C. MASON
*Attesting Officer*

LUTRELLE F. PARKER
*Acting Commissioner of Patents and Trademarks*